United States Patent [19]
Dales et al.

[11] Patent Number: 5,068,458
[45] Date of Patent: Nov. 26, 1991

[54] CHEMICAL PROCESS FOR HALOGENATING 2-METHYL-6-METHOXYNAPHTHALENE

[75] Inventors: John R. M. Dales; Sidney E. Callander, both of Worthing, England

[73] Assignee: Beecham Group p.l.c., Brentford, England

[21] Appl. No.: 545,298

[22] Filed: Jun. 28, 1990

[30] Foreign Application Priority Data

Jun. 30, 1989 [GB] United Kingdom ............ 891510417

[51] Int. Cl.$^5$ ............................................. C07C 41/22
[52] U.S. Cl. ..................................... 568/634; 568/610; 568/631
[58] Field of Search ............... 568/610, 609, 611, 634, 568/631

[56] References Cited

U.S. PATENT DOCUMENTS

| 3,652,683 | 3/1972 | Harrison | 260/612 D |
| 4,408,077 | 10/1983 | Sestanj et al. | 568/441 |
| 4,628,123 | 12/1986 | Borsotti | 568/634 |

FOREIGN PATENT DOCUMENTS 0028725  5/1981  European Pat. Off. ............ 568/610

*Primary Examiner*—Werren B. Lone
*Attorney, Agent, or Firm*—Hopgood, Calimafde, Kalil, Blaustein & Judlowe

[57] ABSTRACT

A process for the preparation of a compound of formula (I):

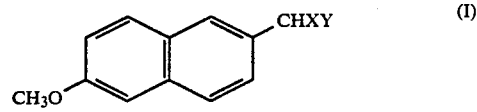

in which X and Y are identical and represent halogen, or X is halogen and Y is hydrogen, which comprises halogenating 2-methyl-6-methoxynaphthalene, of formula (II):

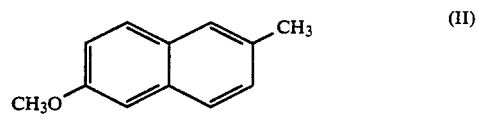

in the presence of a free radical initiator.

5 Claims, No Drawings

CHEMICAL PROCESS FOR HALOGENATING 2-METHYL-6-METHOXYNAPHTHALENE

This invention relates to a novel process for preparing an intermediate compound useful for preparing 4-(6'-methoxy-2'-naphthyl)butan-2-one (hereinafter referred to as nabumetone).

U.S. Pat. No. 4,420,639 describes nabumetone and its use in the treatment of rheumatic and arthritic conditions. A number of processes for preparing the compound are also described in the Patent, one of which proceeds via the intermediate 6-methoxy-2-naphthaldehyde, of formula (A):

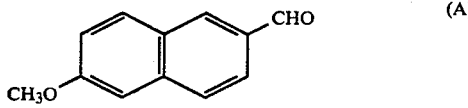

The intermediate of formula (A) may itself be prepared by treating a 6-methoxy-2-halomethyl naphthaldehyde of formula (B):

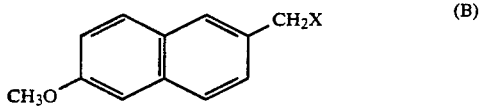

with hexamine in aqueous acetic acid (the Sommelet reaction).

A novel process for the preparation of compounds of formula (B), together with dihalo analogues thereof, has now been devised which utilises free radical catalysed halogenation of a 2-methyl precursor.

According to the present invention, there is provided a process for the preparation of a compound of formula (I):

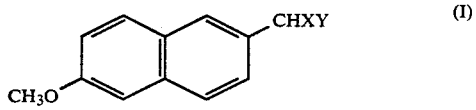

in which X and Y are identical and represent halogen, or X is halogen and Y is hydrogen, which comprises halogenating 2-methyl-6-methoxynaphthalene, of formula (II):

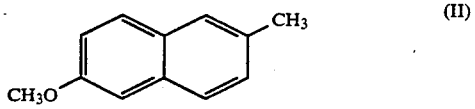

in the presence of a free radical initiator.

The process is preferably carried out in an inert solvent such as carbon tetrachloride and at temperatures from ambient to reflux, preferably reflux.

The term 'halogen' is used herein, to mean chlorine bromine or iodine, preferably bromine.

In order to carry out the halogenation reaction, a conventional halogenating agent may be used, and examples of these are N-halosuccinimide (wherein "halo" is one of chloro, bromo or iodo); 1,3-dihalo-5,5-dimethylhydantoin (wherein "dihalo" is one of dichloror, dibromo or diiodo) and free halogen (e.g., chlorine, bromine or iodine). When the halogen is bromine, the preferred halogenating agent is N-bromosuccinimide.

Examples of free radical initiators include benzoyl peroxide, azoisobutyronitrile and UV light, and the preferred initiator is azoisobutyronitrile.

It has been found advantageous to add a major proportion (ca. 80%) of the free radical initiator to the compound of formula (II) prior to treatment with the halogenating agent, and then to add the halogenating agent together with the remainder of the initiator. The addition of halogenating agent is preferably carried out gradually over a period of up to 3 hours, so as to prevent the occurence of ring halogenation.

In a preferred aspect of the process of the invention, an excess of halogenating agent is employed in order to obtain maximum yield of the di-halo compound of formula (I) (where X and Y are both halo-), which is more easily converted to the compound of formula (A) than is the mono-halo compound of formula (I). By excess, it is meant a molar ratio of N-bromosuccinimide to 2-methyl-6-methoxynaphthalene of >1:1. For example, a favourable yield of the 2-dibromo compound of formula (I) can be obtained by using a molar ratio of N-bromo succinimide to 2-methyl-6-methoxynaphthalene of about 2:1.

As mentioned above, compounds of formula (I) in which X is halogen and Y is hydrogen may be converted to the compound of formula (A) using the Sommelet reaction. However, the conversion may also be carried out using base catalysed hydrolysis to the hydroxy methyl intermediate, followed by oxidation to the aldehyde, or by reaction with dimethyl sulphoxide. Compounds of formula (I) in which X and Y are both halogen may be converted to the compound of formula (A) by hydrolysis such as by treatment with aqueous acetone.

Accordingly, in a further aspect of the invention, a process for preparing 6-methoxy-2-naphthaldehyde comprises halogenating a compound of formula (II), as hereinbefore defined, in the presence of a free radical initiator, and subsequently converting the compound of formula (I) thereby produced to 6-methoxy-2-naphthaldehyde.

Compounds of formula (I) in which X is halogen and Y is hydrogen are known. For example, they are disclosed in the aforementioned US Patent. However, compounds of formula (I) in which X and Y are both halogen are novel, and these form a further aspect of the invention.

The compound of formula (II) is itself known, but may conveniently be prepared by treating the known compound 6-methyl-2-naphthol with dimethyl sulphate in conventional manner.

The invention is illustrated by the following Examples.

EXAMPLE 1

2-Bromomethyl-6-methoxynaphthalene

A solution of 2-methyl-6-methoxynaphthalene (4.1g, 23.8 mmole) and azoisobutyronitrile (80 mg) in dry carbon tetrachloride (30 ml) was heated to reflux with stirring. A slurry of N-bromosuccinimide (4.6 g, 25.8 mmole) and azoisobutyronitrile (20 mg) in dry carbon tetrachloride (10 ml) was added gradually over 2 hours. The resulting solution was heated under reflux for 30 minutes and then cooled to 35° C. The succinimide was filtered off and washed with carbon tetrachloride (5 ml). The filtrate was evaporated to dryness to afford a creamy coloured solid which was dried under vacuum at 40° C. It weighed 5.8 g and contained 70.3% 2-bromomethyl-6-methoxynaphthalene giving an activity yield of 69.5%.

EXAMPLE 2

2-Dibromomethyl-6-methoxynaphthalene

A solution of 2-methyl-6-methoxynaphthalene (4.1 g, 23.8 mmole) and azoisobutyronitrile (80 mg) in dry carbon tetrachloride (30 ml) was heated to reflux with stirring. A slurry of N-bromosuccinimide (8.65 g, 48.6 mmole) and azoisobutyronitrile (40 mg) in dry carbon tetrachloride (15 ml) was added gradually over 2.5 hours. The resulting mixture was heated under reflux for 30 minutes and then cooled to 35° C. The succinimide was filtered off and washed with carbon tetrachloride (35 ml). The filtrate plus washings were cooled to 20° C. and extracted with water (2×15 ml). The organic phase was dried (MgSO₄), filtered and the filtrate evaporated to dryness. The resulting beige solid was recrystallised from dry carbon tetrachloride at +5° C. as cream coloured needles of 2-dibromomethyl-6-methoxynaphthalene. The dried compound weighed 4 g, 52% weight yield, and gave a melting point of 116° C. (darkening).

EXAMPLE 3

Conversion of 2-bromomethyl-6-methoxynaphthalene to

6-Methoxynaphthaldehyde (Sommelet reaction conditions)

A mixture of 2-bromomethyl-6-methoxynaphthalene (12.68 g), hexamine (14 g), glacial acetic acid (21 ml) and water (21 ml) were heated under reflux with stirring for 30 minutes. Concentrated hydrochloric acid (16.6 ml) was then added and the mixture stirred and refluxed for a further 15 minutes. The reaction was cooled to room temperature and extracted with toluene (2×25 ml). The combined toluene extracts were washed with water (2×10 ml), saturated sodium bicarbonate solution (2×10 ml) and water (1×8 ml) and the toluene solution dried over MgSO₄. The drying agent was filtered off and the solvent was removed by distillation under vacuum. This afforded 8.6 g of crude product which was recrystallised twice from isopropanol (2×50 ml) to give 6.07 g of 97.8% purity 2-methoxynaphthaldehyde as a light beige solid. The material had a melting point of 79.2° C.

EXAMPLE 4

Hydrolysis of 2-dibromomethyl-6-methoxynaphthalene to

6-methoxynaphthaldehyde

A solution of 2-dibromomethyl-6-methoxynaphthalene (3 g) in acetone (25 ml) was treated with water (7 ml) and the mixture stirred at 24° C. for 10 hours. The solvent was removed under vacuum and the residue dissolved in toluene (30 ml). The toluene solution was washed with saturated sodium bicarbonate solution (2×10 ml) and water (10 ml) and dried over MgSO₄. The dried solution was filtered and the filtrate evaporated down to a yellowish-brown semi-solid. This was recrystallised twice from isopropanol (2×10 ml) to give 0.5 g of pure 2-methoxynaphthaldehyde as confirmed using HPLC (conditions; spheresorb $C_{18}$ 25 cm×4.5 mm i.d. (column), 65% acetonitrile/35% water (eluent), 1 ml/min (flowrate), 310 nm (wavelength). The samples were dissolved in acetonitrile and 20 μl injected onto the column. The retention time for 2-methoxynaphthaldehyde was about 6 minutes.

We claim:

1. A process for the preparation of a compound of formula (I):

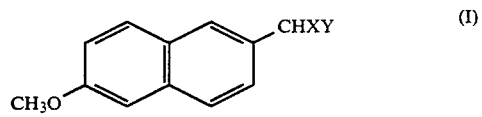

in which X and Y are identical and represent bromine or chlorine or X is bromine or chlorine and Y is hydrogen, which comprises brominating or chlorinating 2-methyl-6-methoxynaphthalene, of formula (II):

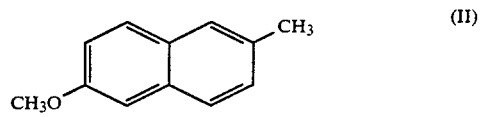

in the presence of a free radical initiator.

2. A process according to claim 1 wherein the brominating agent is an N-bromo succinimide, 1,3-dibromo-5-5-dimethylhydantoin or free bromine or the chlorinating agent is an N-chlorosuccinimide, 1,3-dichloro-5-5-dimethylhydantoin or free chlorine.

3. A process according to claim 1, wherein the free radical initiator is one of benzoyl peroxide, azoisobutyronitrile or UV light.

4. A process according to claim 1, wherein the addition of brominating or chlorinating agent is carried out gradually over a period of up to 3 hours.

5. A process according to claim 1, wherein an excess of brominating or chlorinating agent is employed.

* * * * *

UNITED STATES PATENT AND TRADEMARK OFFICE
CERTIFICATE OF CORRECTION

PATENT NO. : 5,068,458
DATED : November 26, 1991
INVENTOR(S) : John R.M. Dales et al.

It is certified that error appears in the above-identified patent and that said Letters Patent is hereby corrected as shown below:

On the Title page,

The priority data should read as follows:

Item [30]   Foreign Priority Data
    June 30, 1989 [GB] United Kingdom ----8915104.7--

Signed and Sealed this

Twenty-fifth Day of May, 1993

Attest:

MICHAEL K. KIRK

*Attesting Officer*   Acting Commissioner of Patents and Trademarks